United States Patent [19]

Malinowski

[11] Patent Number: 5,453,087

[45] Date of Patent: Sep. 26, 1995

[54] HANDPIECE FOR CATARACT SURGERY

[76] Inventor: Igor Malinowski, 955 Deep Valley Dr., Box No. 2981, Palos Verdes Estates, Calif. 90274

[21] Appl. No.: 158,686

[22] Filed: Nov. 26, 1993

Related U.S. Application Data

[63] Continuation-in-part of Ser. No. 918,551, Jul. 15, 1992, abandoned.

[51] Int. Cl.$^6$ .................................................. A61B 17/20
[52] U.S. Cl. ................................................................ 604/22
[58] Field of Search .................. 604/19–22; 606/59, 606/169–171; 607/111–116; 601/21

[56] References Cited

U.S. PATENT DOCUMENTS

| | | | |
|---|---|---|---|
| 4,169,984 | 10/1979 | Parisi | 604/22 |
| 4,609,368 | 9/1986 | Dotson, Jr. | 604/22 |
| 4,741,731 | 5/1988 | Starck et al. | 604/22 |
| 4,804,364 | 2/1989 | Dieras et al. | 604/22 |
| 5,151,084 | 9/1992 | Khek | 604/22 |
| 5,178,605 | 1/1993 | Imonti | 604/22 |
| 5,211,625 | 5/1993 | Sakurai et al. | 604/22 |

*Primary Examiner*—C. Fred Rosenbaum
*Assistant Examiner*—N. Kent Gring
*Attorney, Agent, or Firm*—Lewis B. Sternfels

[57] ABSTRACT

An ultrasonic handpiece for cataract surgery comprises a driver assembly (10), a housing (11), a nose part (13, 113) and an end or rear manifold (20) of one-piece construction. Housing (11) includes tubular parts (12, 12' and 14), which are concentrically assembled and attached to and between nose part (13, 113) and rear or end manifold (20). Nose part (13, 113) is provided with a plurality of integral front irrigation holes (19) and end manifold (20) with a plurality of integral irrigation holes (36a, 36b and 36c). The number and inclinations of the irrigation holes permit and maintain a uniform, gradual and substantially unimpeded and high volume flow of irrigation fluid from an irrigation luer fitting (2) into the annular space between tubular parts (12, 12' and 14), resulting in a fluid flow concentric with driver assembly (10) and inside housing (11), thus eliminating any need for external irrigation tubes of conventional handpieces. In one embodiment, outer tube (12, 12') is also capable of being completely removed from the unit comprising nose part (113), inner tube (14) and rear manifold (20) and this unit's internally sealed driver assembly (10), to permit full cleansing of the outer surface of inner tube (14) and the inner surface of outer tube (12, 12') while maintaining the fluid-tight integrity of driver assembly (10).

14 Claims, 3 Drawing Sheets

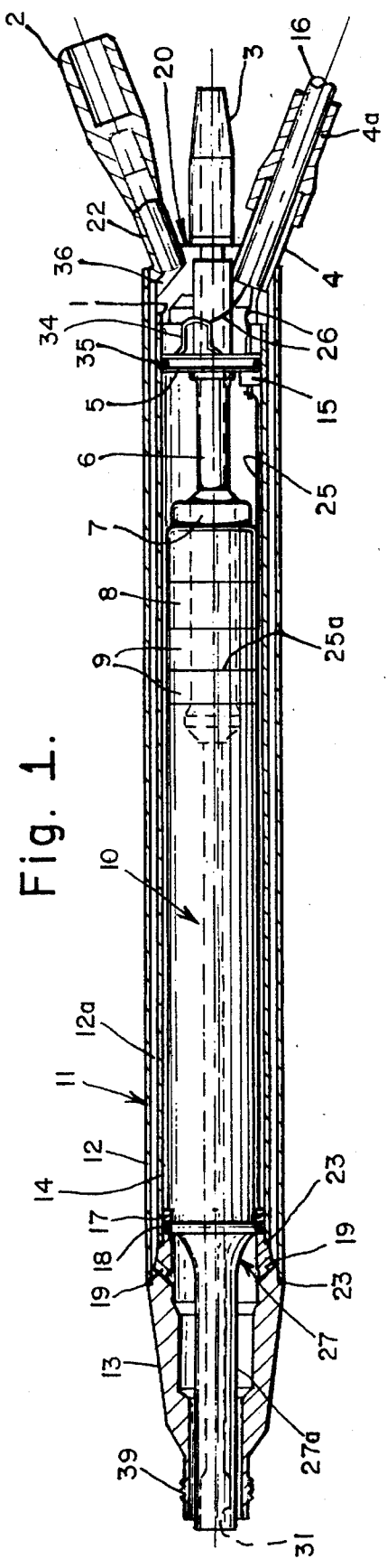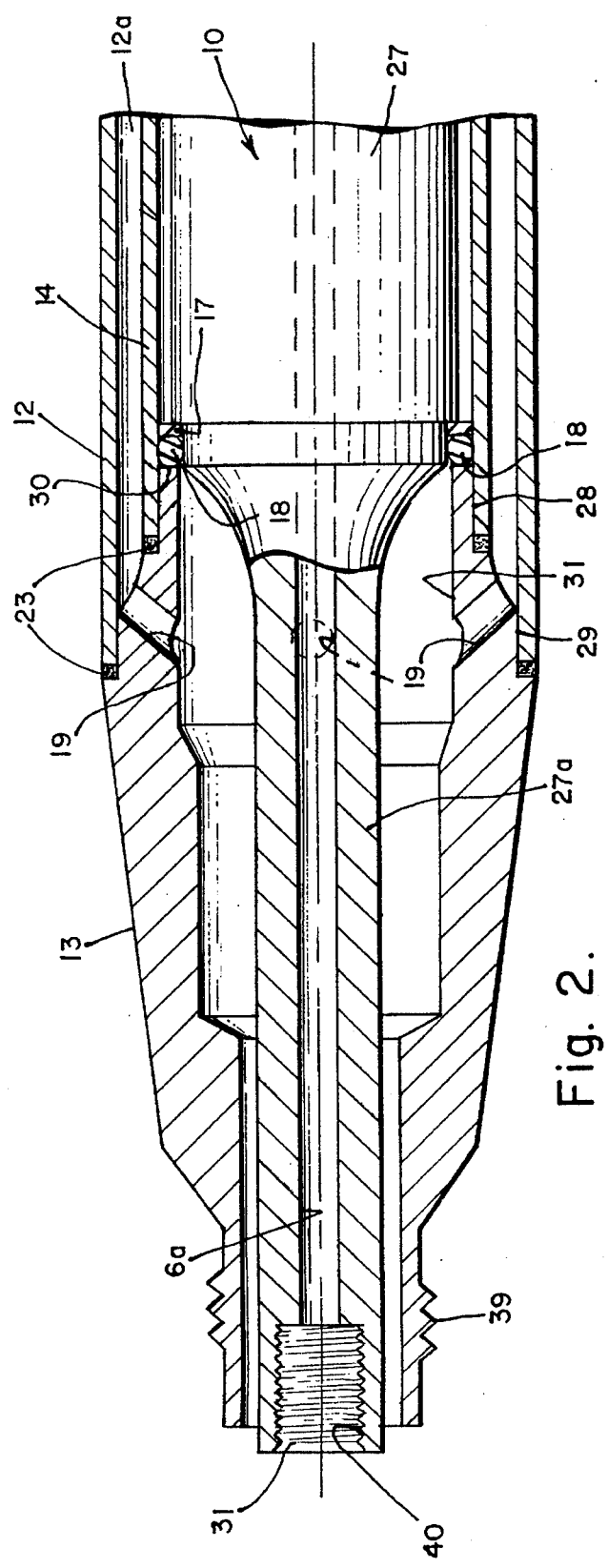
Fig. 1.
Fig. 2.

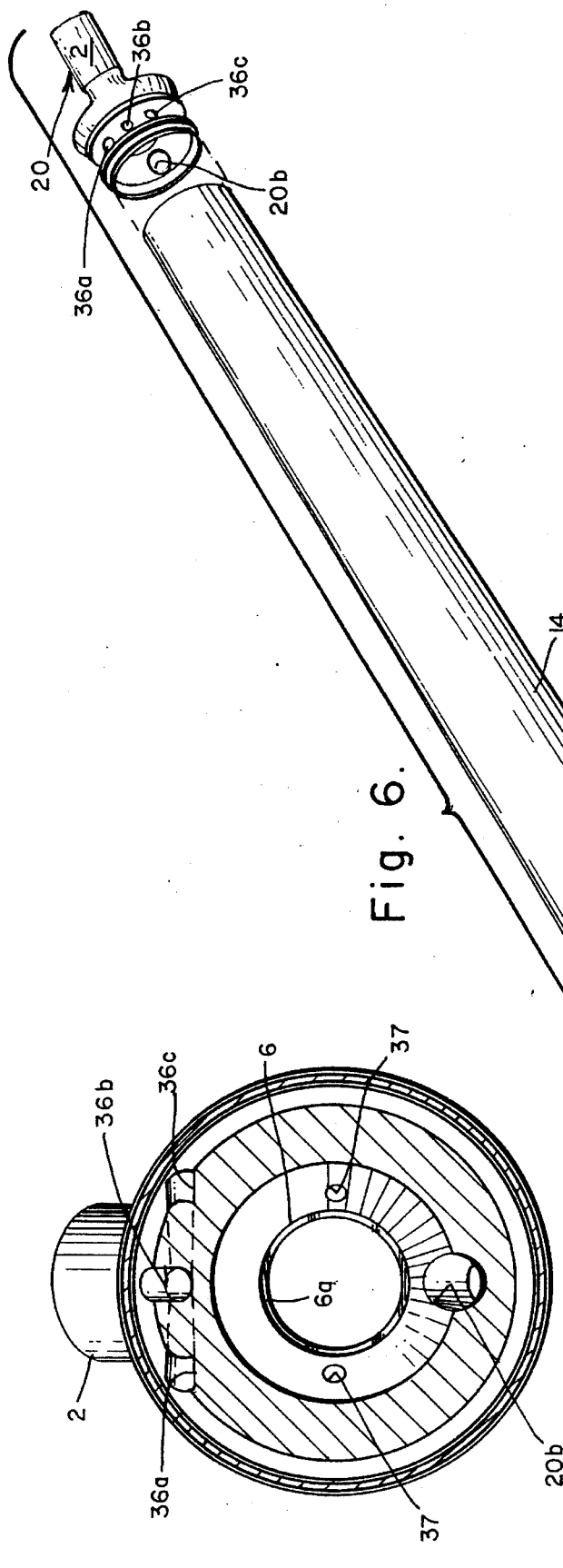
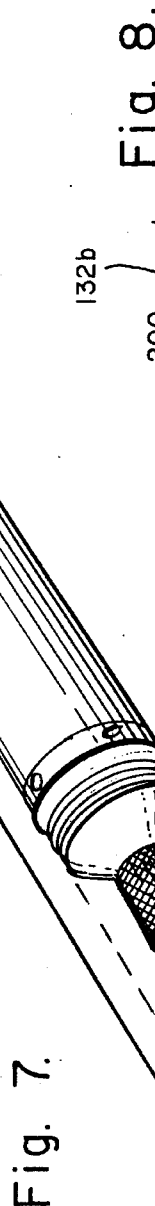
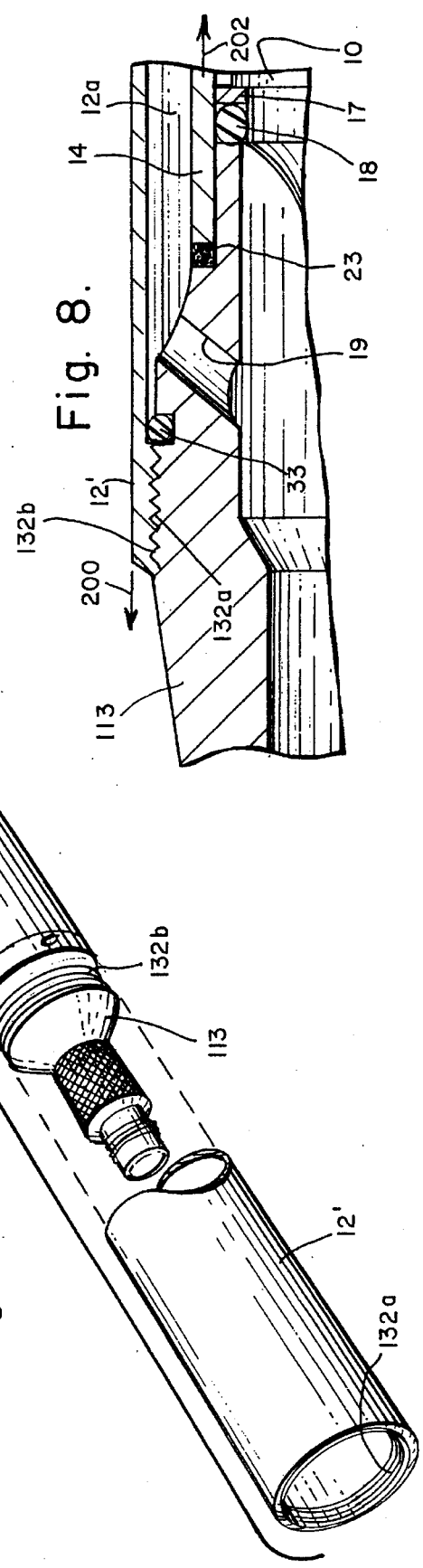
Fig. 6.
Fig. 7.
Fig. 8.

HANDPIECE FOR CATARACT SURGERY

This is a continuation-in-part of application, Ser. No. 07/918,551 filed 15 Jul. 1992, now abandoned.

BACKGROUND OF THE INVENTION

1. Field of the Invention

The present invention relates in general to handpieces for cataract surgery and, in particular, to ultrasonic handpieces which can be easily cleaned and provide improved and more efficient routing of fluids through irrigation and aspiration channels to and from a patient's eye.

2. Description of Related Art and Other Considerations

A typical ultrasonic handpiece used in ophthalmic surgery includes a housing, an ultrasonic driver assembly centered within the housing, a rear part or cap at one end of the housing, a front part with a cataract needle at the other end of the housing, and an irrigation conduit extending between the front and the rear parts.

The rear part furnishes irrigating fluid to the front part for supply to the eye, receives the fluid after being flushed through the eye, and seals about an electrical connection between the driver assembly and an exterior source of power. The front part with a cataract needle is adapted to penetrate the patient's eye for supplying ultrasonic vibrations thereto and for channelling the fluid into and out of the eye.

An external tube may be attached to the exterior of the housing, or an annular space may be provided between concentrically arranged tubular shells disposed about the ultrasonic driver assembly. Irrigation tubes exterior to the housing are known to interfere with the surgeon's fingers during operation. While ultrasonic handpieces with concentrically arranged tubular shells avoid this problem, they and the exterior tubes are subject to other problems.

It is important that the irrigating fluid flow as evenly and uniformly as possible, and at a sufficiently rapid rate so as to ensure removal of the fragmented lens from the patient's eye, and at a sufficiently high pressure to prevent collapse of the eye during the surgery, as is known and required by practitioners using and manufacturers of such ophthalmic instruments. It is further important that the handpiece be easily cleaned, without wetting or otherwise harming its driver assembly, in particular.

SUMMARY OF THE INVENTION

The present invention avoids the aforementioned problems and otherwise meets the above criteria by employing improved irrigation flow and disassembly of handpiece for the purpose of cleaning, without harm to its driver assembly.

The handpiece of the present invention includes outer and inner concentric tubes joined at one end by a novel rear manifold. The tubes permit flow of the irrigation fluid internally within the handpiece, to avoid use of an irrigation tube external to the housing. Further, the rear manifold and front needle part respectively have streamlined passages to improve flow of the fluid by encouraging relatively unimpeded flow of the irrigation fluid to and from the annular space defined by the two concentric tubes.

In one embodiment of the present invention, the driver assembly is sealed within the inner tube by and between the front part and the rear manifold to form a fluid-tight unit. This fluid-tight sealed unit can thus be removed from within the outer tube for enabling the respective surfaces of the disassembled inner and outer tubes to be cleaned without exposing the driver assembly to the hazards of being harmed in any manner, such as by being wetted by the fluid or cleaning materials.

Several advantages are obtained from the above constructions, for example, improved flow of irrigation fluid through and ease of disassembly and reassembly of the handpiece.

The arrangement, which improves flow of irrigation fluid in the annular channel between two concentric tubular surfaces, allows the handpiece to have a round outside shape and, consequently, permits the surgeon to more easily hold and rotate the handpiece in his/her fingers.

The improved flow of irrigation fluid around the inner tube and its internally sealed driver assembly permits enhanced cooling of such ultrasonic driver elements as its piezoelectric crystals and horn, which typically heat up during operation of the handpiece, and also permits cooling of the outer surface of the handpiece.

The improved concentric flow of the irrigation fluid additionally provides a uniform and enhanced flow to assure removal of the fragmented lens from the patient's eye and, more importantly, sufficient pressure within the eye to prevent its collapse during the surgical operation.

The relatively small outside diameter to horn diameter ratio of the handpiece permits the use of an ultrasonic horn of maximum diameter for a given outside diameter of the housing. The simple construction of the handpiece utilizes a small number of constituent parts, such as a housing comprising a single metallic part and a one-part rear end manifold of metal or plastic, resulting in a construction which is durable, uncomplicated and inexpensive.

Simple sealing techniques in the end manifold portion of the handpiece result in improved sealing as compared with the use of other techniques utilized in the manufacture of conventional handpieces. With regard to avoiding use of an external irrigation tube which, as stated above, precludes interference with the physician's fingers, also avoids more expensive costs of manufacturing associated with the handpiece having the external irrigation tube.

Further objects and advantages of the present invention will become apparent from a study of the drawings and description thereof described hereinafter.

BRIEF DESCRIPTION OF THE DRAWINGS

FIG. 1 illustrates an axial cross-sectional view of a first embodiment of a handpiece of the present invention;

FIG. 2 shows an enlarged partial cross-section of the nose part of the embodiment depicted in FIG. 1;

FIG. 6 is a perspective view of another embodiment of the present invention, illustrating its ability to be disassembled, e.g., to facilitate cleaning of the handpiece;

FIG. 7 is a view of the end manifold of either embodiment depicted in FIGS. 1 and 6; and FIG. 8 is an enlarged partial cross-section of the connection which permits disassembly of the embodiment depicted in FIG. 6.

Figure 3:
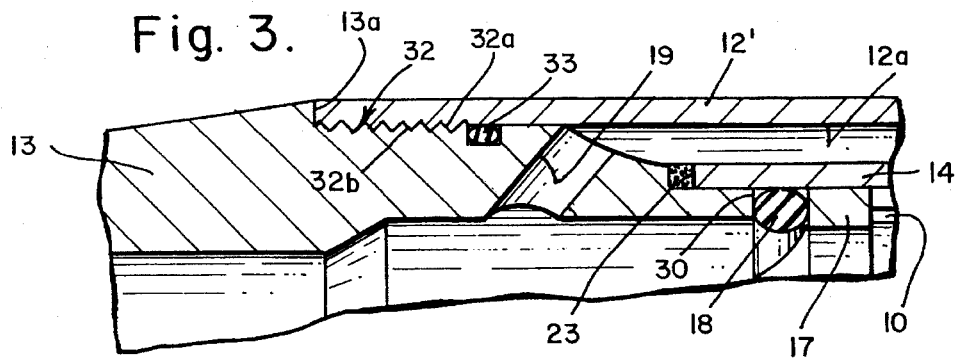
FIG. 3 shows an enlarged partial cross-section of an alternate of the nose part illustrated in FIG. 2.

Reference numerals in drawing figures:

The ultrasonic handpiece for cataract surgery of the present invention comprises the following parts:

1 - inner, back O-ring seal for manifold 20
2 - irrigation luer fitting
3 - aspiration luer connector
4 - connecting tube
4a - strain relief
5 - bulkhead
6 - locating bolt
6a - aspiration bore, path
7 - back nut
8 - spacer
9 - piezoelectric crystals
10 - driver assembly
11 - handpiece housing
12 - outer tube, FIGS. 1 and 2
12' - outer tube, FIGS. 3 and 8
12a - annular space between tubes 12, 12' and 14
13 - nose part
13a - abutment on nose part 13 of tube 12', FIG. 3
14 - inner tube
15 - insulator
16 - power cable
17 - washer
18 - front O-ring
19 - front irrigation holes
20 - end or rear manifold
20a - opening in manifold 20
20b - opening in manifold 20
21 - outer, back O-ring seal for manifold 20
22 - irrigation connector
23 - weld or solder seam
24 - O-ring seal for locating bolt 6
25 - ribbon electrical connector
25a - electrode
26 - electrical wires
26a - electric conduit in insulator 15
27 - horn
27a - front part of horn 27
28 - smaller cylindrical surface on part 13
29 - larger cylindrical surface on part 13
30 - abutment surface on nose part 13 for O-ring 18
31 - clearance bore in nose part 13
32 - front, threaded connection between tube 12' and nose part 13
32a - internal thread on outer tube 12'
32b - external thread on nose part 13
33 - front, O-ring for nose part 13
34 - ground connector.
35 - O-ring in bulkhead 5
36 - irrigation holes in manifold 20
36a - irrigation hole
36b - irrigation hole
36c - irrigation hole
37 - assembly holes
38 - central hole in manifold 20
39 - external mounting thread on nose 13
40 - front internal thread of horn 27
42 - rear decoupling sleeve in manifold 20
113 - nose part
132a - internal thread on outer tube 12'
132b - external thread on nose part 113
200 - direction of travel of tube 12' with respect to nose part 113
202 - direction of travel of nose part 113 with respect to tube 12'

DETAILED DESCRIPTION OF THE PREFERRED EMBODIMENTS

FIG. 1 depicts an axial cross-section through a typical ultrasonic handpiece embodying the present invention. All dimensions, materials and processes given herein are intended as examples for a specific handpiece and, therefore, are presented for purposes of illustration and not limitation.

As shown also in FIGS. 2 and 3, a handpiece housing 11 comprises inner tubes 12 and 12' concentrically placed about and inner tube 14 which form an annular space or path 12a between their facing surfaces. Outer and inner tubes 12, 12' and 14 are affixed to a nose part 13 which, as shown in FIG. 2, comprise two water-tight or fluid-tight connections 23 that may be formed by brazing, silver soldering, or laser or particle beam welding or which, as illustrated in FIG. 3, may be effected by a single braze, silver or welded connection 23 and a threaded connection 32 coupled with an O-ring 33. In FIG. 3, threaded travel of tube 12' on nose part 13 is limited by contact of an end of tube 12' with an abutment 13a on the nose part. A front O-ring seal 33 resides in a groove on nose part 13, and is sealed against the cylindrical bore of tubes 12 and 12'. The nose part is, for example, of stainless steel, and is made typically by means of turning and drilling. The outside diameter of nose part 13 is 12.7 mm. and the length is on the order of 25 mm. and can be adjusted to the length of other components.

As best seen in FIG. 2, nose part 13 has a clearance bore 31 for a front part 27a of a horn 27. The diameter of clearance bore 31 is typically 4.6 mm. Additionally, nose part 13 has two concentric cylindrical surfaces 28 and 29. Larger surface 29, whose diameter typically is 11.9 mm., serves to locate outer tube 12. Smaller cylindrical surface 28 serves to locate inner tube 14.

A plurality of front irrigation holes 19 are formed solely within nose part 13, such as by drilling, and have diameters on the order of 1.3 mm. and are positioned intermediate surfaces 28 and 29. By locating holes 19 solely within nose part 13, it is possible to control their opening sizes and slopes and the gradualness thereof and, thus, to maximize the uniformity and relatively smooth and unimpeded fluid flow therethrough. Holes 19 serve to connect annular space or path 12a between tubes 12, 12' and 14 with bore 31 with a minimum of fluid friction. Typically, there are two to six front irrigation holes 19 in nose part 13 to establish proper irrigation and rate of flow.

The nose part has an external mounting thread 39 to which is attached an irrigation sleeve (not shown) of conventional type, used for cataract surgery. Thread 39 is typically a ¼-32 UNF machine thread.

Figure 4:
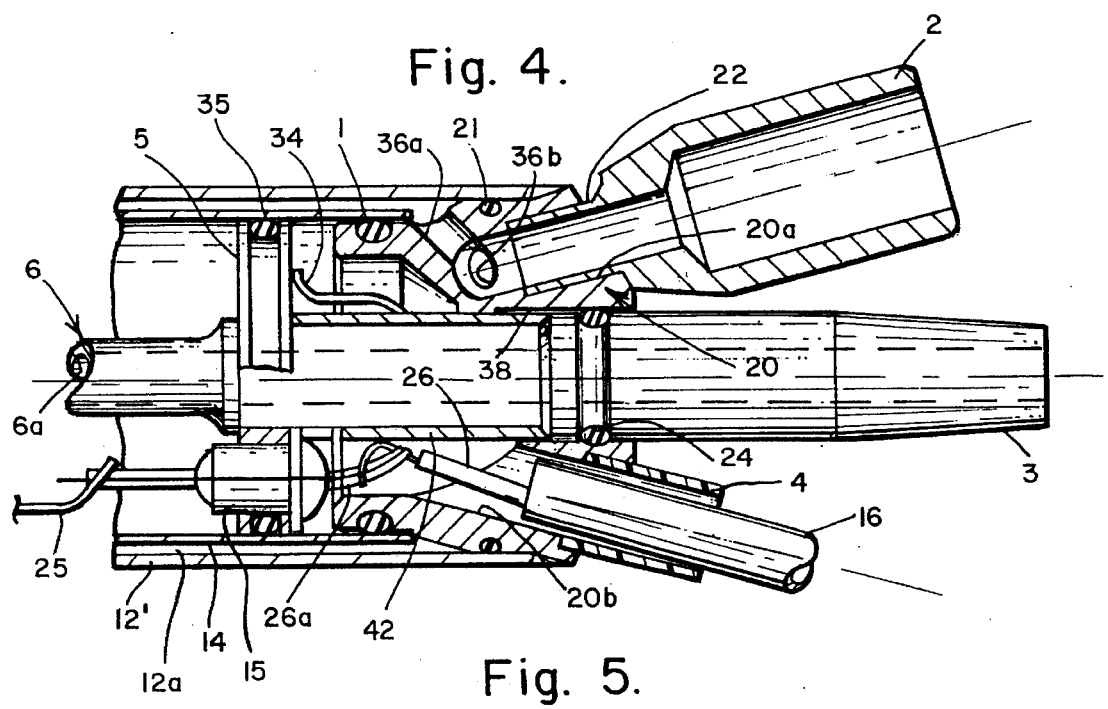
FIG. 4 shows a partial cross-section of a slightly modified form of the end manifold of the embodiment shown in FIG. 1.

As best shown in FIG. 4, an end or rear manifold 20 is positioned at the back of the handpiece. The manifold is provided with a unitary construction and is fabricated, for example, from stainless steel, such as 304 series steel, or from an injection molded plastic, such as Ultem (a trademark of General Electric Company for a polyethermide resin). Manifold 20 is connected to tubes 12, 12' and 14 by press fitting and by O-ring seals 1 and 21.

Inner back O-ring seal 1, located in a groove in end manifold 20, seals inner tube 14 to end manifold 20.

Outer back O-ring seal 21, which is similarly located in a groove in end manifold 20, seals outer tubes 12 and 12' to end manifold 20. O-ring seals 1 and 21 are of conventional construction and are typically made of silicone rubber, with O-ring seal 1 being 1.5 mm. and O-ring 21 being 1 mm. in diameter.

End manifold 20 is provided with an opening 20a for coupling the manifold to a source of irrigation fluid. In FIG. 1, an irrigation connector 22 is inserted within opening 20a and connected, by means of a press fitting and brazing or silver soldering, with the end manifold. Irrigation connector 22 is typically made of stainless steel tubing. In FIG. 4, connector 22 is integrated with irrigation luer fitting 2.

Connector 22 is further connected to an irrigation luer fitting 2 by means of brazing or silver soldering or another conventional method of joining metals. Luer fitting 2 is made to meet ANSI standard MD 70.1-1983 female luer taper, whose angle is 1 degree, 43 minutes, 6 seconds.

A plurality of back irrigation holes or openings 36, typically three holes 36a, 36b and 36c (see FIGS. 6 and 7, in addition to FIG. 4), are formed by drilling or other suitable means in end manifold 20. Openings 36a, 36b and 36c are configured to define slopes that are oblique and obtuse to the interior wall of outer tube 12 and thereby permit these openings to merge gradually into annular space 12a. Therefore, openings 36a, 36b and 36c provide a gradual fluid connection between irrigation luer fitting 2 and annular space 12a between tubes 12, 12' and 14. This gradual and sloping fluid connection provided by holes 36a, 36b and 36c assure a substantially uniform and unimpeded fluid flow and, like holes 19, reduces impediments and friction to fluid flow and increases the rate of flow over that provided by conventional handpieces. A useful diameter of back irrigation holes 36 is 1.2 mm.

Opposite to irrigation connector 22, a connecting tube 4 is attached by press fitting and brazing to an opening 20b in manifold 20. The diameter of connecting tube 4 is 3.2 mm. A strain relief 4a (see FIG. 1), typically made from a section of flexible, silicone plastic tubing, is attached to connecting tube 4 by expanding the diameter of relief 4a and fitting it over the connecting tube.

An electrical cable 16 is fitted through an opening in strain relief 4a and connecting tube 4 into end or rear manifold 20.

A plurality of electrical wires 26, which are a part of electrical cable 16, are attached to a ground connector 34 and to an electrical conduit 26a passing through an insulator 15. The conduit in insulator 15 is coupled by electrical wires 25 to a plurality of piezoelectric crystals 9 shown in FIG. 1. Insulator 15 is a feedthrough insulator of conventional design.

Insulator 15 is inserted in and retained in position in a bulkhead 5. An O-ring 35 is placed about bulkhead 5 and seals off an internal area of the handpiece within inner tube 14 for housing piezoelectric driver crystals 9 in a fluid-tight environment. Bulkhead 5 may also be attached to inner tube 14 by silver soldering, brazing or other conventional joining methods, which further allows for grounding of an electric charge. Also, as illustrated in FIG. 1, a driver assembly 10 is placed inside inner tube 14.

Driver assembly 10 is of the type conventionally used in handpieces for cataract surgery and is used to amplify the oscillations of piezoelectric crystals 9. Other types of ultrasonic driver elements which have been used previously in handpieces for cataract surgery, may be used instead of the piezoelectric crystals, such as a magneto-restrictive system.

Driver assembly 10 comprises a horn 27, a locating bolt 6 threaded into horn 27, two or more piezoelectric crystals 9 separated by an electrode 25a and placed around locating bolt 6, a spacer 8 also placed around bolt 6 and a nut 7 surrounding and threaded to bolt 6. The function of nut 7 is to apply pressure on crystals 9.

Piezoelectric crystals 9 may be insulated by a layer of an insulating tape wrapped around them and a part of horn 27. The insulating tape used for insulating crystals 9 may comprise a polyimide insulating tape of conventional manufacture.

Horn 27 is typically formed from a titanium-aluminum-vanadium alloy, such as one generally known in the trade as Ti6Al4V, and has a tapered shape at its front part 27a to amplify oscillations from crystals 9. The outside diameter of horn 27 is 9.5 mm. Horn 27 has in its front section an internal thread 40 which is used to attach a cataract needle (not shown) to the horn. Thread 40 is typically #40-80 UNS 2 B machine thread to accommodate standard cataract needles.

As shown in FIGS. 1 and 2, driver assembly 10 is held within the front end of the handpiece by an O-ring 18 and a washer 17 in the bore of tube 14, and within the back end of the handpiece by bulkhead 5. The bulkhead and bolt 6 may be attached together by brazing, silver soldering or other suitable method. O-ring seal 18 is of a conventional type and its diameter is on the order of 1.5 mm.

FIG. 4 shows a partial cross-sectional view of end manifold 20 in an alternative embodiment using a rear decoupling sleeve. Locating bolt 6 passes through a central hole 38 in end or rear manifold 20. O-ring seal 24 provides a seal between central hole 38 of end manifold 20 and aspiration luer fitting 3.

One or more of O-ring seals 24 (see FIG. 4) are assembled over a back portion of locating bolt 6. Each O-ring seal 24 is of conventional type having a diameter on the order of 0.7 mm.

As also best shown in FIG. 4, an aspiration luer fitting 3 is attached to the end portion of locating bolt 6 by means of brazing, silver soldering or thread joint. Fitting 3 is typically made of stainless steel such as a 304 type and is made to comply with ANSI standard MD 70.1-1983.

Ground connector 34 is attached by spot welding or brazing to bulkhead 5. Bulkhead 5 accommodates O-ring 35 and insulator 15, which is soldered to bulkhead 5.

Cable 16 is fed through connecting tube 4. Cable 16 contains individual wires 26 which are connected to the electrical conduit in insulator 15 and ground connector 34.

A rear decoupling sleeve 42 is placed over the rear end of locating bolt 6 and within hole 38 of manifold 20. Sleeve 42 is typically made of flexible, silicone polymeric tubing.

Sleeve 42 permits the use of a sealant other than the flexible RTV mentioned earlier, to electrically insulate and seal the opening between bulkhead 5, end manifold 20 and inner tube 14. It is advantageous to use an epoxy potting compound to insulate the wires because the dielectric constant of epoxy is higher than that of the silicone RTV compound. The problem of applying of an epoxy potting compound lays in the rigidity of epoxy. Since the epoxy is more rigid than silicone RTV, it does not tolerate well the vibrations occurring at the end of locating bolt 6. The use of soft, silicone rear decoupling sleeve 42 permits it to deform under the oscillations of bolt 6, with the rest of the area, which is filled with epoxy potting compound being insulated from oscillations. The higher dielectric constant of the epoxy potting compound permits a better electrical insulation of the electrical leads inside of the space between end manifold 20 and bulkhead 5. Such improved insulation prolongs the life of the handpiece and postpones electrical breakdown of the RTV insulation, which is responsible for short life of existing handpieces in the field.

Figure 5:
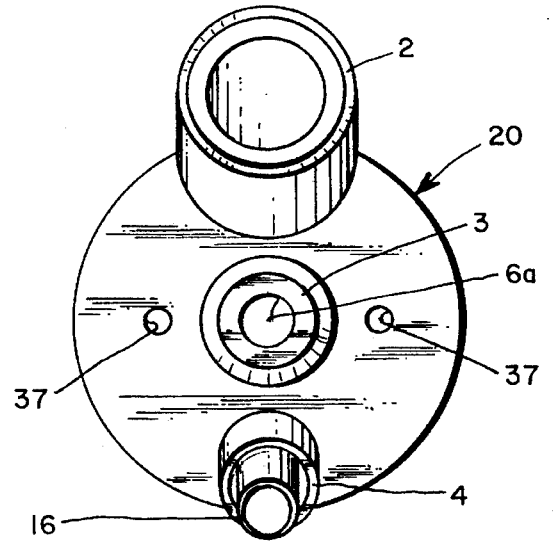
FIG. 5 shows a back view of the end manifold of the embodiment shown in FIG. 1.

FIG. 5 shows the back view of end manifold 20. Irrigation luer fitting 2 is located above aspiration luer fitting 3. Connecting tube 4, with its strain relief 4a and cable 16 are located below aspiration luer 3. Assembly holes 37 are made in rear or end manifold 20 to allow filling of the space in the end manifold with a sealant, such as the RTV sealant manufactured by General Electric or Dow Corning or an epoxy potting mixture mentioned in the alternative embodiment described with respect to FIG. 4.

Assembly of the handpiece of the present invention:

The typical process of assembly of a handpiece for eye surgery of the present invention is described below.

Driver assembly 10 is preassembled in a conventional way by threading locating bolt 6 into horn 27 and placing a plurality (typically two) of piezoelectric crystals 9, separated by an electrode, over bolt 6. Spacer 7 is placed over bolt 6 and is compressed, together with crystals 9, by tightening nut 7 over the threads of locating bolt 6. Ribbon connector 25 is fully insulated with the previously mentioned polyimide insulating tape which, as stated above, is wrapped around crystals 9 and a part of horn 27. The end of the electrode is soldered to electrical conduit 26a of insulator 15. Crystals 9 are insulated with polyimide tape, also as mentioned before. O-ring seal 35 is assembled over the groove in bulkhead 5 and O-ring seal 24 is placed near aspiration luer connector 3 over bolt 6.

Prior to insertion of horn 27 into housing 11, O-ring seal 18 and washer 17 are placed over the front part of horn 27. Since housing 11 utilizes a flow over the entire surface of inner tube 14, a cooling action of liquid might cause condensation of water on the inside walls of the inner tube. Because of this reason, it is recommended that the inside of housing 11 be flushed with a dry nitrogen, dry air, or other non-flammable, non-toxic gas not containing easily condensing vapors, during assembly of driver assembly 10 into housing 11.

The flushing with gas may be done in a following simple way. A hose, connected at one end to a nitrogen tank, is connected with threads 39 of nose part 13 of housing 11. Nitrogen is then released and flows from nose part 13 through inner tube 14. Once nitrogen has pushed all air out, an assembly of horn 27 may take place.

When driver assembly 10 is pushed into housing 11, it presses washer 17 against O-ring seal 18 and seats seal 18 firmly against an abutment surface 30 on nose part 13. Seal 18 is thus compressed and, as a consequence thereof, is forced and sealed against the internal diameter of inner tube 14 and with driver assembly 10 in a fluid-tight engagement. O-ring seal 35 is similarly compressed between bulkhead 5 and inner tube 14, to provide a fluid-tight seal at that point. Thus, the interior of the handpiece and its driver assembly 10 are maintained fluid-tig rom fluids flowing between tubes 12, 2' and 14. Bulkhead 5 may be soldered with inner tube 14 for better sealing. After soldering of the bulkhead, the dry nitrogen flush may be used to purge any moisture from the areas where electrical connections had been made.

In the next step, end manifold 20 is assembled by brazing or silver soldering connector 22 to it, followed by a similar assembly of irrigation luer fitting 2 to connector 22, as shown in FIG. 1. Alternatively, as illustrated in FIG. 4, luer fitting 2, which is made as one part with connector 22, is similarly affixed to the manifold. In a like manner, connecting tube 4 is silver soldered or brazed to end manifold 20. O-ring seals 1 and 21 are placed over their respective grooves in end manifold 20. Strain relief 4a is placed over cable 16 and connecting tube 4. Cable 16 is routed through the opening in connecting tube 4 into the opening in end manifold 20. Appropriate wires of cable 16 are soldered to ground connector 34 and to electrical conduit 26a of insulator 15.

End manifold 20 is then pushed into housing 11. O-ring seal 1 is compressed by inner tube 14 and O-ring seal 21 is compressed by outer tubes 12 and 12'. Strain relief 4a is moved over and extends outwardly from connecting tube 4. A silicone sealant is injected into one of holes 37 to fill the space between bulkhead 5 and end manifold 20, until excess sealant extrudes through other hole 37.

Operation of the present invention:

The manner of using the present invention is typical for ultrasonic handpieces for cataract surgery.

In preparation for cataract surgery, a hollow, metallic cataract needle of conventional type (not shown) is threaded onto threads 40 in the front part of horn 27. An irrigation sleeve of conventional type (not shown) is placed over the needle and over a front portion of nose part 13 to control the flow of irrigation liquid into the patients eye. An aspiration hose of conventional type is connected to aspiration luer fitting 3 and an irrigation hose is connected to irrigation luer fitting 2. Aspiration and irrigation hoses (not shown) are of conventional types used for cataract surgery and connect the handpiece to a console (not shown) containing a control computer, driver circuitry and fluidics systems.

The console is conventional and contains a fluidics system to control the flow of irrigation fluid to and from the eye. The console contains also an electrical ultrasonic driver and a functional control system. The function of an ultrasonic driver is to apply electrical impulses to drive piezoelectric crystals 9 of the handpiece. The ultrasonic driver is connected with the handpiece through cable 16. A physician, prior to cataract surgery, holds the handpiece so that its needle points upwardly, to cause the irrigation fluid to flow for a short period of time and to remove any air which might have been trapped inside the irrigation channel. During the same time, the ultrasonic driver adjusts the frequency of oscillations to the most appropriate level for a given handpiece. The functional control system during the same time checks electrical condition of the handpiece.

During cataract surgery, the surgeon inserts the cataract needle into the lens of the patients eye through a small incision therein. Ultrasonic vibration of the needle applied by crystal 9 allow parts of the eye's lens to fragment along the path of the needle. The fragmented lens parts are removed together with the irrigation fluid by vacuum applied from the console using aspiration path 6a through the center of the needle, horn 27, locating bolt 6 and luer fitting 3 into the console, in a way conventional for phacoemulsification surgery.

Controlled flow of the irrigation fluid fills the void created by the removal of fragmented parts of the lens and helps to cool the needle and other parts of the handpiece.

Also, during the cataract surgery, the console controls flow of the irrigation fluid through the irrigating hose (not shown), to irrigation luer fitting 2 and connector 22, and into the plurality of irrigation holes 36. The use of more than one irrigation hole 36, typically three irrigation holes, allows fluid to be guided with minimal losses from irrigation connector 22 to space 12a between tubes 12, 12' and 14. The exit points of holes 36 into the space between tubes 12, 12' and 14 are typically positioned on the perimeter of end manifold 20, with one hole 36b, as shown, being located in the plane of cross-section, while the two other holes 36a and 36b are located symmetrically on both sides of hole 36b previously described to streamline and thus improve fluid flow into and through the annular space between tubes 12, 12' and 14.

Such an arrangement permits all irrigation holes 36 to originate near irrigation connector 22 and to end in various points on the perimeter of end manifold 20 in the space between tubes 12, 12' and 14. Such a design helps the irrigation fluid to be evenly distributed into space 12a between tubes 12, 12' and 14 and allows losses of flow of the irrigation fluid to be minimized; thus, the performance of the present invention matches or exceeds that of conventional handpieces which utilize an external irrigation tube.

The irrigation fluid thence flows through front irrigation holes 19 into bore 31 of nose part 13 around the front part of horn 27. Further fluid flows around the horn into an irrigation sleeve around the cataract needle. The fluid exits into the patient's eye in a conventional way through holes in the irrigation sleeve, located on its perimeter.

The fluid is removed from the eye together with the fragmented parts of the lens through the bores or aspiration path 6a of the cataract needle, horn 27, locating bolt 6 and aspiration luer fitting 3.

From fitting 3, fluid is removed through the aspiration hose into the console, where it is pumped into a container.

Reference is now directed to FIGS. 6–8, which depict substantially the same handpiece as that illustrated in FIGS. 1–5, with the important improvement that enables the handpiece to be cleaned between its outer and inner tubes 12, 12' and 14. Those elements of the handpiece, which are the same between the two embodiments, utilize the same reference numerals, while the changes in structure employ new reference numerals.

Accordingly, a nose part 113 terminates inner tube 14 in the same manner as that described with respect to those elements illustrated in FIGS. 1–3. Nose part is coupled to outer sleeve or tube 12' through a threaded connection 132, comprising internal threads 132a at one end of outer tube 12' and external threads 132b on nose part 113. However, unlike nose part 13 of FIG. 3, which has an abutment 13a, there is no such abutment on nose part 113. This omission of the abutment permits outer tube 12' to be removed completely from inner tube 14 and nose part 113, in the opposite directions as respectively depicted by arrows 200 and 202.

Therefore, the handpiece can be disassembled by unscrewing and fully sliding outer tube 12' from the unit comprising nose part 113, inner tube 14 and rear manifold 20 and this unit's internally sealed driver assembly 10. While in this disassembled condition, the outer surface of inner tube 14 and the inner surface of outer tube 14 can be cleaned and any deposits, which might otherwise impede flow of the irrigating fluid, can be removed. During cleaning, the integrity of the sealing and fluid-tight environment of the driver assembly housed within the unit is maintained.

After the respective tube surfaces are cleaned and inspected, outer tube 12' is then slid back over nose part 113 and inner tube 14, and screwed securely in place on the nose part by re-engaging threads 132a and 132b.

While the above description contains many specifics, these should not be construed as limitations on the scope of the present invention, but rather as examples of its preferred embodiments. Other variations are possible, such as the manufacture of the housing and the end manifold out of materials other than stainless steel, or the use of other manufacturing techniques such as casting and sintering, or the placement of bulkhead 5 or an additional equivalent adjacent nose part 13.

Accordingly, the scope of the present invention should be determined not by the embodiments illustrated, but by the appended claims and their legal equivalents.

What is claimed is:

1. A housing for a handpiece for eye surgery comprising:

a nose part;

a rear manifold;

an inner tube;

an outer tube surrounding said inner tube to form a space therebetween for allowing flow of an irrigating fluid therethrough, said inner and outer tubes being attached at their respective ends to said nose part and said manifold;

aspiration bore means extending through said front nose part, said tubes and said rear manifold;

a driver assembly housed within said inner tube and having front and rear portions;

a first fluid-tight attachment respectively secured to and between said manifold and said tubes;

a second fluid-tight attachment respectively secured to and between nose part and said tubes;

a third fluid-tight attachment between said driver assembly rear portion and said inner tube, said first, second and third fluid-tight attachments forming a fluid-tight interior bounded by said nose part, said manifold and said inner tube for said driver assembly therein, said second fluid-tight attachment including a threaded connection for permitting said nose part, said manifold and said inner tube, as a unit, to be removed from said outer tube, said fluid-tight joints of said rear portion and said second fluid-tight attachment ensuring the fluid-tight integrity of said fluid-tight interior and said driver assembly therein independent of said first fluid-tight attachment between said manifold and said tubes.

2. A housing for an ultrasonic handpiece for eye surgery comprising:

a nose part;

a rear manifold;

concentric inner and outer tubes which have an annular space therebetween for allowing flow of an irrigating fluid therethrough and which are attached in first and second structural and fluid-tight junctures respectively to and between said nose part and said manifold and thereby for forming a fluid-tight interior bounded by said nose part, said manifold and said inner tube; and an ultrasonic driver assembly having front and rear portions, said front portion having a fluid-tight joint with said nose part and said inner tube at said first juncture, and said rear portion having a fluid-tight joint with said inner tube adjacent said second juncture, said junctures between one of (a) said nose part and said outer tube and (b) said manifold and said outer tube including means for permitting the other of (c) said nose part and said inner tube and (d) said manifold and said inner tube, as a unit, to be removed from said outer tube, said fluid-tight joints of said front and rear portions ensuring the fluid-tight integrity of said fluid-tight interior and said ultrasonic driver assembly therein independent of said second juncture between said manifold and said inner and outer tubes.

3. A housing according to claim 2 in which said nose part includes surfaces attached respectively to said inner and outer tubes, and a plurality of irrigation holes positioned solely in said nose part and between said nose part surfaces for permitting flow of the fluid out of the annular space between said tubes.

4. A housing according to claim 2 in which said manifold comprises a unitary construction and includes:

first and second surfaces attached by fluid-tight joints respectively to said inner and outer tubes, with said fluid-tight joint at said first surface being positioned behind said fluid-tight joint between said rear portion and said inner tube and separated thereby from said driver assembly; and a plurality of irrigation holes solely in said manifold and positioned between said manifold surfaces for permitting flow of the fluid into the annular space between said tubes.

5. A housing according to claim 4 in which said manifold further includes means defining a fluid source opening for coupling said manifold to a source of the irrigation fluid, means defining a plurality of openings coupled between said fluid source opening means and the annular space between said tubes and having a configuration that is oblique to that of said outer wall and thereby provides a path for a substantially uniform and unimpeded flow of the fluid into the annular space.

6. A housing according to claim 5 in which the configuration define slopes that enter into the annular space at angles which are obtuse to outer tube and thereby permit said plurality of opening means to merge gradually into the annular space.

7. A housing for an ultrasonic handpiece for eye surgery comprising:

a nose part;

a rear manifold;

concentric inner and outer tubes which have an annular space therebetween for allowing flow of an irrigating fluid therethrough and which are attached in first and second structural and fluid-tight junctures respectively to and between said nose part and said manifold and thereby for forming a fluid-tight interior bounded by said nose part, said manifold and said inner tube; and an ultrasonic driver assembly having front and rear portions, said front portion having a fluid-tight joint with said nose part and said inner tube at said first juncture, and said rear portion having a fluid-tight joint with said inner tube adjacent said second juncture, said first juncture between said nose part and said outer tube including a threaded connection for permitting said nose part, said manifold and said inner tube, as a unit, to be removed from said outer tube, said fluid-tight joints of said front and rear portions ensuring the fluid-tight integrity of said fluid-tight interior and said ultrasonic driver assembly therein independent of said second juncture between said manifold and said inner and outer tubes.

8. A housing according to claim 7 wherein said rear portion of said driver assembly includes a bulkhead, and further including a permanent attachment between said bulkhead and said inner tube.

9. A housing according to claim 8 further including a sealant bonding said bulkhead, said inner tube and said manifold together.

10. An ultrasonic handpiece for eye surgery comprising:

a housing including a front nose part, a rear manifold, and concentric inner and outer tubes attached to and between said nose part and said manifold and arranged to form an annular space therebetween;

means defining an aspiration bore extending through said front nose part, said tubes and said rear manifold;

first and second fluid-tight seals respectively between said tubes and said end manifold and between said aspiration bore means and said end manifold;

a third fluid-tight seal between said aspiration bore means and at least said inner tube;

a bulkhead secured in fluid-tight engagement with said aspiration bore means and said inner tube adjacent at least one of said nose part and said rear manifold;

an ultrasonic driver assembly supported by said aspiration bore means within said inner tube and between said bulkhead and said nose part for thereby being secured in a fluid-tight environment;

said nose part having a plurality of irrigation holes therein and positioned intermediate said tubes for flow of fluid therethrough from the annular space for irrigating an eye; and said end manifold having a unitary construction, and including means defining an opening for receiving said aspiration bore means and means defining a plurality of irrigation holes communicating with the annular space to permit fluid flow thereto one of (a) said nose part and said outer tube and (b) said manifold and said outer tube including connections for permitting the other of (c) said nose part and said inner tube and (d) said manifold and said inner tube, as a unit, to be removed from said outer tube, said fluid-tight engagement of said bulkhead and said aspiration bore means and said third fluid-tight seal ensuring the fluid-tight environment within said inner tube and said ultrasonic driver assembly therein independent of said first fluid-tight seal between said manifold and said inner and outer tubes.

11. A housing according to claim 10 further including a permanent attachment between said bulkhead and said inner tube.

12. A housing according to claim 11 further including a sealant bonding said bulkhead, said inner tube and said manifold together.

13. An ultrasonic handpiece for eye surgery comprising:

a housing including a front nose part, a rear manifold, and concentric inner and outer tubes attached to and between said nose part and said manifold and arranged to form an annular space therebetween;

means defining an aspiration bore extending through said front nose part, said tubes and said rear manifold;

first and second fluid-tight seals respectively between said tubes and said end manifold and between said aspiration bore means and said end manifold;

a third fluid-tight seal between said aspiration bore means and at least said inner tube;

a bulkhead secured in fluid-tight engagement with said aspiration bore means and said inner tube adjacent at least one of said nose part and said rear manifold;

an ultrasonic driver assembly supported by said aspiration bore means within said inner tube and between said bulkhead and said nose part for thereby being secured in a fluid-tight environment;

said nose part having a plurality of irrigation holes therein and positioned intermediate said tubes for flow of fluid therethrough from the annular space for irrigating an eye; and said end manifold having a unitary construction, and including means defining an opening for receiving said aspiration bore means and means defining a plurality of irrigation holes communicating with the annular space to permit fluid flow thereto said nose part and said outer tube including a threaded connection for permitting said nose part, said manifold and said inner tube, as a unit, to be removed from said outer tube, said fluid-tight engagement of said bulkhead and said aspiration bore means and said third fluid-tight seal ensuring the fluid-tight environment within said inner tube and said ultrasonic driver assembly therein independent of said first fluid-tight seal between said manifold and said inner and outer tubes.

14. A housing according to claim 13 further including a permanent attachment between said bulkhead and said inner tube, and a sealant bonding said bulkhead, said inner tube and said manifold together.

* * * * *